United States Patent [19]

Chang et al.

[11] 4,025,575

[45] May 24, 1977

[54] PROCESS FOR MANUFACTURING OLEFINS

[75] Inventors: Clarence D. Chang, Princeton; William H. Lang, Pennington, both of N.J.

[73] Assignee: Mobil Oil Corporation, New York, N.Y.

[22] Filed: Apr. 8, 1975

[21] Appl. No.: 566,166

[52] U.S. Cl. .................................. 260/682
[51] Int. Cl.² ............................... C07C 1/20
[58] Field of Search ...................... 260/682

[56] References Cited
UNITED STATES PATENTS

| | | | |
|---|---|---|---|
| 3,894,106 | 7/1975 | Chang et al. | 260/682 |
| 3,894,107 | 7/1975 | Butter et al. | 260/668 R |
| 3,911,041 | 10/1975 | Kaeding et al. | 260/682 |
| 3,928,483 | 12/1975 | Chang et al. | 260/668 R |
| 3,931,349 | 1/1976 | Kuo | 260/668 R |

*Primary Examiner*—C. Davis
*Attorney, Agent, or Firm*—Charles A. Huggett; Vincent J. Frilette

[57] ABSTRACT

A lower alcohol and/or ether feed is selectively converted to a mixture of light olefins, including ethylene and propylene, by catalytic contact of the feed, for example methanol or dimethyl ether, at subatmospheric partial pressure, with certain crystalline aluminosilicate zeolite catalysts exemplified by HZSM-5.

19 Claims, No Drawings

PROCESS FOR MANUFACTURING OLEFINS

BACKGROUND OF THE INVENTION

1. Field of the Invention

This invention is concerned with the manufacture of light olefin hydrocarbons from lower alcohols on their ethers. It is particularly concerned with the catalytic conversion of such alcohols and ethers selectively to mixtures of olefins having up to five carbon atoms. In another aspect, this invention is concerned with a novel catalytic process especially effective for the substantially complete conversion of methanol and/or dimethyl ether to a hydrocarbon mixture characterized by a predominance of olefins.

2. Description of the Prior Art

A remarkable growth in the production of synthetic fibers, plastics and rubber has taken place in recent decades. This growth, to a very large extend, has been supported and encouraged by an expanding supply of inexpensive petrochemical raw materials such as ethylene, propylene, and other, four and five carbon olefins. Side by side with this remarkable development, there has been an increasing demand for alkylate, made by reacting olefins with isobutane, for use as a high octane gasoline component. Environmental factors which limit the lead content of gasoline are likely to aggravate the need for alkylate.

Burgeoning demand for olefins, particularly ethylene, propylene and butenes, has of course led to periods of shortage, either due to short supply of suitable feedstocks or to limited processing capacity. In any case, it would appear desirable to provide efficient means for converting raw materials other than petroleum to olefins. The dehydration of alcohols, particularly ethanol to ethylene, by catalytic contact with the hydrogen exchanged form of mordenite is disclosed in U.S. Pat. No. 3,244,766 issued Apr. 5, 1966.

The production of olefins from methanol and dimethyl ether by limited conversion with HZSM-5 zeolite catalyst is described in copending U.S. Pat. application Ser. No. 537,043 filed Dec. 27, 1974, and now abandoned.

The use of a hydrocarbon diluent to dissipate exothermic heat in a two-stage conversion of methanol to gasoline is described in U.S. Pat. No. 3,931,349 issued Jan. 6, 1976 to Kuo.

A two-stage conversion of methanol to olefins and to gasoline which employs a tubular reactor for the second stage is described in U.S. patent application Ser. No. 496,434 filed Aug. 9, 1974 and now abandoned.

BRIEF SUMMARY OF THE INVENTION

In a preferred embodiment of the present invention, a feed comprising one or more compounds, selected from the lower monohydric alcohols with up to four carbon atoms and their simple or mixed either derivatives, is substantially completely converted, to a mixture comprising a major fraction of light olefins, by contact at subatmospheric partial pressure with a particular type of crystalline aluminosilicate catalyst hereinafter described. Generally, the mixture of olefins produced by this invention, even with a single alcohol feed, contains mostly ethylene, propylene, and the butylenes with a small pentenes component.

The alcohols may be manufactured from synthesis gas, i.e. a mixture of CO and $H_2$ made from coal or from natural gas, or they may be produced by fermentation, or they may be manufactured from petroleum fractions in excess supply. The olefin hydrocarbons produced may be converted to alkylate or to aromatics and blended with gasoline, or they may be separated and used as petrochemicals. Thus, in one aspect, the present invention provides a novel means for producing hydrocarbon petrochemicals and fuels from raw materials other than petroleum.

As noted above, the mixture of olefins produced by this invention contains mostly ethylene, propylene, and the butylenes with a small pentenes component. This appears to be so regardless whether one feeds methanol, dimethyl ether, ethanol or other permissible feeds as defined elsewhere herein. Thus, it is characteristic of this invention to produce a "conjunct mixture" of olefins, i.e. a product composition unrelated to the exact nature of the feed and from which the feed cannot be recognized. Thus, the conversion of this invention clearly differs from classical dehydration wherein the olefin produced bears a simple relation to the alcohol charged.

In the present invention, it is critical to conduct the conversion at subatmospheric partial pressure of reactant feed in order to achieve substantially complete conversion of the feed with maximum olefin yield. Subatmospheric partial pressure of the reactant feed is obtained either by maintaining a partial vacuum in the conversion zone or by cofeeding a diluent. The utilization of a particular type catalyst, exemplified by HZSM-5, is also critical.

DETAILED DESCRIPTION OF THE INVENTION

Any composition comprising one or more alcohol or ether compounds that have the structural formula $(C_nH_{2n+1})-O-(C_mH_{2m+1})$ wherein $n = 1$ to 4 and $m = 0$ to 4 may be used as reactant feed to the process of this invention. Thus, methanol, ethanol, normal propanol, isopropanol, normal butanol, secondary butanol, isobutanol and tertiary butanol may be used either alone or in admixture with one another, or in admixture with simple ethers of the above alcohols such as dimethyl ether. Likewise, mixed ethers derived from these alcohols, such as methyl-ethyl ether, may be used. It will be noted that all of the compounds indicated have the structural formula above described. Preferred reactant feeds are methanol, dimethyl ether and mixtures thereof, and the above-described compositions that contain at least 10% methanol or dimethyl ether by weight. For the purpose of this invention, the feed need not be of greater than ordinary technical purity. It is an attribute of this invention that other oxygenated compounds such as esters and the like that may be present in the feed, will often convert to hydrocarbons along with the alcohols.

The production of olefins by catalytic conversion of lower alcohols at one atmosphere and higher pressures is disclosed in copending U.S. patent application Ser. No. 537,043, filed Dec. 27, 1974. As shown therein, a catalyst similar to that used in the present invention is employed. Also as disclosed therein, however, it is necessary to severely restrict the fraction converted of the feed to avoid production of aromatic and paraffin hydrocarbons instead of olefins, thus necessitating separation of olefins and recycle of unconverted feed to achieve high olefin yields. Similar conversions employing two or more stages of reaction are disclosed in U.S. patent application Ser. No. 496,434, now abandoned, and Ser. No. 508,113, now U.S. Pat. No. 3,931,349.

The surprising discovery of the present invention, that selectivity for olefin production from alcohol feed is greatly enhanced by conversion at subatmospheric partial pressure referred to alcohol, permits substantially complete conversion of the alcohol to hydrocarbons without recycle. It is to be understood, of course, that reference to a subatmospheric partial pressure as used herein means the partial pressure of the feed, measured or calculated at the maximum temperature that obtains within the reactor and conversion occurs. Thus, a specified partial pressure at the inlet of a reaction zone, the inlet being defined as the location where feed first encounters catalyst; or an inlet partial pressure of the feed; or the maximum feed partial pressure within a reaction zone, are to be understood as alternative ways to identify the same quantity. Also, it is to be clearly understood that all references to partial pressure, as used herein, are to be understood as "partial pressure referred to alcohol". Thus, if a pure, single ether is charged, its partial pressure referred to alcohol will be twice its actual partial pressure. Thus, regardless of whether an alcohol or its simple ether are fed at the same specified partial pressure, all else being the same, the olefins produced in both cases will in turn be at the same partial pressures.

Any subatmospheric inlet partial pressure of the feed, i.e. any inlet partial pressure of the feed less than 15 p.s.i.a., i.e., 15 pounds per square inch absolute, produces some improvement of selectivity for olefin production compared with operation at an inlet partial pressure of 15 p.s.i.a. or higher. The selectivity improvement generally occurs at the expense of a lower yield of aromatic and/or paraffin hydrocarbons. However, selectivity improvement increases as the inlet partial pressure decreases, and the maximum advantage is derived from this invention by operation at an inlet partial pressure not more than about 12 p.s.i.a. The preferred range for the inlet partial pressure of the feed is about 0.1 p.s.i.a. to about 12 p.s.i.a., with the range of about 0.8 p.s.i.a. to about 7.5 p.s.i.a. particularly preferred.

The inlet partial pressure of the feed, referred to alcohols, may be maintained at not more than about 12 p.s.i.a. i.e. pounds per square inch absolute pressure, either by maintaining the reactor under partial vacuum or by adding an appropriate amount of a diluent to the feed. The diluents that may be used include any substantially inert substance that is a gas or vapor at reaction temperature. Gaseous nitrogen, carbon dioxide, carbon monoxide hydrogen and steam are examples of such materials. Steam offers the advantage of easy separation from product olefins, but may decrease the activity of the catalyst somewhat under certain conditions. Hydrogen should not be used under such conditions that will promote hydrogenation of product olefins. Paraffin hydrocarbons having from one to eight carbon atoms, preferably from 1 to 5 carbon atoms, may be used. Methane and ethane are substantially inert under the reaction conditions of this process, especially at the higher space velocities. The other hydrocarbons from propane through pentanes are refractory to conversion under most of the reaction conditions described more fully hereinbelow. Hydrocarbon diluents may be supplied from the by-products of the alcohol and/or ether conversion; it is important that the diluents be substantially free of olefins.

It will be recognized that when diluents are used the total pressure in the reaction zone may range from subatmospheric up to about 1500 p.s.i.a., depending on the amount of diluent introduced with the feed. It is a feature of this invention that the diluent serves to assist in removing the heat of reaction generated in the more exothermic alcohol or ether conversions, i.e. with the preferred methanol and dimethyl ether feeds. The preferred total pressure in the reaction zone, when using diluents, is 15 p.s.i.a. to 500 p.s.i.a.

In the process of this invention, the temperature in the reaction zone may be from about 500° F to about 1000° F, with the preferred range of about 600° F to about 900° F. Particularly preferred is the range of about 650° F to about 850° F.

The feed may be passed over the catalyst at a rate in the range of 0.05 to 200 L.H.S.V. (Liquid Hourly Space Velocity, i.e. liquid volumes of feed per volume of catalyst per hour). It is preferred, however, to operate in the range of about 1 L.H.S.V. to about 50 L.H.S.V. Although the advantage provided by this invention of producing olefins with improved selectivity is not negated by operating under a combination of conditions which does not convert all of the feed, it is most advantageous to select the combination of temperature, feed rate and inlet partial pressure conditions such that at least 85 weight percent of the feed is converted to hydrocarbons, and it is particularly preferred to select the combination of conditions so that substantially complete feed conversion is in fact achieve. Furthermore, it is particularly advantageous to use conditions in the specified ranges that produce conversion to a hydrocarbon mixture comprising a major fraction by weight of olefins. While it is difficult to precisely specify the conditions to accomplish this because of the varying reactivity of the different feeds, in general the use of the lower values up to about 7.5 p.s.i.a. of the above-specified range of inlet partial pressures of the feed together with feed rates in the range of about 1.0 L.H.S.V. to about 20 L.H.S.V. will produce this very desirable result.

It is critical for the purpose of this invention to use certain crystalline zeolites as the active catalysts. The catalysts referred to are members of a special class of zeolites exhibiting some unusual properties . These zeolites induce profound transformations aliphatic hydrocarbons to aromatic hydrocarbons in commercially desirable yields and are generally highly effective in alkylation, isomerization, disproportionation and other reactions involving aromatic hydrocarbons. Although they have unusually low alumina contents, i.e. high silica to alumina ratios, they are very active even with silica to alumina ratios exceeding 30. This activity even with silica to alumina ratios exceeding 30. This activity is surprising since catalytic activity of zeolites is generally attributed to framework aluminum atoms and cations associated with these aluminum atoms. These zeolites retain their crystallinity for long periods in spite of the presence of steam even at high temperatures which induce irreversible collapse of the crystal framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from, the intra-crystalline free space by virtue of having a pore dimension greater than about 5 Angstroms and pore windows of about a size such as would be provided by 10-membered rings of oxygen atoms. It is to be understood, of course, that these rings are those formed by the regular disposition of tetrahedra making up the anionic framework of the crystalline aluminosilicate, the oxygen atoms themselves being bonded to the silicon or aluminum atoms art the centers of the tetrahedra. Briefly, the zeolites useful in this invention possess, in combination: a silica to alumina ratio of at least about 12; and a structure providing constrained access to the crystalline free space.

The silica to alumina ratio referred to may be determined by conventional analyis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 40. It is particularly preferred to use zeolites having a silica to alumina ratio of at least 70. Such zeolites, after activation, acquire an intracrystalline sorption capacity for normal hexane which is greater than that for water, i.e., they exhibit "hydrophobic" properties. It is believed that this hydrophobic character is advantageous in the present invention.

The zeolites catalysts used in this invention freely sorb normal hexane and have a pore dimension greater than about 5 Angstroms. In addition, their structure must provide constrained access to some larger molecules. It is sometimes possible to judge from a known crystal structure whether such constrained access exists. For example, if the only pore windows in a crystal are formed by 8-membered rings oxygen atoms, then access by molecules of larger cross-section than normal hexane is substantially excluded and the zeolite is not of the desired type. Zeolites with windows of 10-membered rings are preferred, although excessive puckering or pore blockage may render these zeolites substantially ineffective. Zeolites with windows of twelve-membered rings do not generally appear to offer sufficient constraint to produce the advantageous conversions desired in the instant invention, although structures can be conceived, due to pore blockage or other cause, that may be operative.

Rather than attempt to judge from crystal structure whether or not a zeolite possesses the necessary constrained access, a simple determination of the "constraint index" may be made by continuously passing a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F for at least 15 minutes. The zeolite is then flushed with helium and the temperature adjusted between 550° F and 950° F to give an overall conversion between 10 and 60%. The mixture of hydrocarbons is passed at 1 liquid hourly space velocity (i.e., 1 volume of liquid hydrocarbon per volume of catalyst per hour) over the zeolite with a helium dilution to give a helium to total hydrocarbon mole ratio of 4:1. After 20 minutes on stream, a sample of the effluent is taken and analyzed, most conveniently by gas chromotography, to determine the fraction remaining unchanged for each of the two hydrocarbons.

The constraint index is calculated as follows:

$$\text{Constraint Index} = \frac{\log_{10} \text{ (fraction of n-hexane remaining)}}{\log_{10} \text{ (fraction of 3-methylpentane remaining)}}$$

The constraint index approximates the ratio of the cracking rate constants for the two hydrocarbons. Catalysts suitable for the present invention are those which employ a zeolite having a constraint index from 1.0 to 12.0. Constraint Index (CI) values for some typical zeolites including some not within the scope of this invention are:

| CAS | C.I. |
|---|---|
| ZSM-5 | 8.3 |
| ZSM-11 | 8.7 |
| ZSM-35 | 4.5 |
| TMA Offretite | 3.7 |
| ZSM-12 | 2 |
| ZSM-38 | 2 |
| Beta | 0.6 |
| ZSM-4 | 0.5 |
| Acid Mordenite | 0.5 |
| REY | 0.4 |
| Amorphous Silica-alumina | 0.6 |
| Erionite | 38 |

The above-described Constraint Index is an important and even critical, definition of those zeolites which are useful to catalyze the instant process. The very nature of this parameter and the recited technique by which it is determined, however, admit of the possibility that a given zeolite can be tested under somewhat different conditions and thereby have different constraint indexes. Constraint Index seems to vary somewhat with severity of operation (conversion). Therefore, it will be appreciated that it may be possible to so select test conditions to establish multiple constraint indexes for a particular given zeolite which may be both inside and outside the above defined range of 1 to 12.

Thus, it should be understood that the Constraint Index value as used herein is an inclusive rather than an exclusive value. That is, a zeolite when tested by any combination of conditions within the testing definition set forth herein above to have a constraint index of 1 to 12 is intended to be included in the instant catalyst definition regardless that the same identical zeolite tested under other defined conditions may give a constraint index value outside of 1 to 12.

The class of zeolites defined herein is exemplified by ZSM-5, ZSM-11, ZSM-12, ZSM-21, ZSM-35, ZSM-38 and other similar material. Recently issued U.S. Pat. NO. 3,702,886 describing and claiming ZSM-5-is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

U.S. appliction, Ser. No. 358,192, filed May 7, 1973, and now abandoned, the entire contents of which are incorporated herein by reference, describes a zeolite composition, and a method of making such, designated as ZSM-21 which is useful in this invention.

U.S. application Ser. No. 528,061 filed Nov. 29, 1974, the entire contents of which are incorporated herein by reference, describes a zeolite composition including a method of making it. This composition is designated ZSM-35 and is useful in this invention.

U.S. application Ser. No. 528,060 filed Nov. 29, 1974, and now abandoned, the entire contents of which are incorporated herein by reference, describes a zeolite composition including a method of making it. This composition is designated ZSM-38 and is useful in this invention.

The x-ray diffraction pattern of ZSM-21 appears to be generic to that of ZSM-35 and ZSM-38.

The specific zeolites described, when prepared in the presence of organic cations, are substantially catalytically inactive, possibly the intracrystalline free space is occupied by organic cations from the forming solution. They may be activated by heating in an inert atmosphere at 100° F for 1 hour, for example, followed by base exchange with ammonium salts followed by calcination at 100° F in air. The presence of organic cations in the forming solution may not be absolutely essential to the formation of this special type zeolite; however, the presence of these cations does appear to favor the formation of this special type of zeolite. More generally, it is desirable to activate this type zeolite by base exchange with ammonium salts followed by calcination in air at about 100° F for from about 15 minutes to about 24 hours.

Natural zeolites may sometimes be converted to this type zeolite by various activation procedures and other treatments such as base exchange, steaming, alumina extraction and calcination, alone or in combinations. Natural minerals which may be so treated include ferrierite, brewsterite, stilbite. dachiardite, epistilbite, heulandite and cliniptilotlite. The preferred crystalline aluminosilicates are ZSM-5, ZSM-11, ZSM-12 and ZSM-21, ZSM-35 and ZSM-38 with ZSM-5 particularly preferred.

The zeolites used as catalysts in this invention may be in the hydrogen form or they may be base exchanged or impregnated to contain ammonium or a metal cation complement. It is desirable to calcine the zeolite after base exchange. The metal cations that may be present include any of the cations of the metals of Groups I through VIII of the periodic table. However, in the case of Group IA metals, the cation content should in no case be so large as to substantially eliminate the activity of the zeolite for the catalysis being employed in the instant invention. For example, a completely sodium exchanged H-ZSM-5 appears to be largely inactive for shape selective conversions required in the present invention.

In a preferred aspect of this invention, the zeolites useful as catalysts herein are selected as those having a crystal framework density, in the dry hydrogen form of not substantially below about 1.6 grams per cubic centimeter. It has been found that zeolites which satisfy all three of these criteria most desired, Therefore, the preferred catalysts of this invention are those comprising zeolites having a constraint index as defined above of about 1 to 12, a silica to alumina ratio of at least about 12 and a dried crystal density of not substantially less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meier. this paper, the entire contents of which are incorporated herein by reference, is included in "Proceedings of the Conference on Molecular Sieves, London, April, 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density of course must be associated with a relatively with a relatively small amount of free space within the crystal, which might be expected to result in more stable structures. This free space, however, seems to be important as the locus of catalytic activity.

Crystal framework densities of some typical zeolites including some which are not within the purview of this invention are:

| Zeolite | Void Volume | Framework Density |
| --- | --- | --- |
| Ferrierite | 0.28 cc/cc | 1.76 g/cc |
| Mordenite | .28 | 1.7 |
| ZSM-5,-11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

For the purpose of this invention, the catalyst may be in any conventional form such as pellets, beads, or extrudate. Binders such as clays, alumina and silica-alumina may be present.

Contact of the feed with the solid catalyst in the process of this invention may be carried out by passing the feed through a bed of the catalyst. The catalyst bed may be any of the fixed, fixed fluid, or transported bed types. In a fixed or moving bed operation, the average particle size of the catalyst may be as great as one-half inch or more, but is generally between about one-sixteenth and one-fourth inch in diameter. If a fluid bed is employed, the catalyst must be in finely divided form which can be fluidized by the lifting action of the feed and diluent vapors. Transport type catalyst beds, such as those used in fluid catalytic cracking, may be used.

The effluent from the catalystic conversion step is treated by conventional means to segregate the mixture of olefins to the desired degree, this depending on the specific intended use of one or more of the olefin products.

The following examples are illustrative of various aspects of the invention without being limiting on the scope thereof. Parts and percentages are by weight unless expressly stated to the contrary.

EXAMPLES 1-11

HZSM-5 extrudate catalyst containing 35% alumina binder was charged to a stainless steel reactor equipped with electrical resistance heaters adjusted to control the reaction temperature at about 800° F. The HZSM-5 used has a silica to alumina ratio of 70. Methanol was passed over the catalyst at a specified L.H.S.V. by means of a positive displacement pump. Mass flow meters were used to feed gases. Liquid and/or gas products were collected in wet and dry ice traps. Gas product, when less than 5 liters total, was collected directly into an evacuated calibrated system. In high gas dilution runs, the effluent from the reactor was scrubbed through a liquid nitrogen trap and measured with a wet test meter. At the end of the run, condensed gases in the nitrogen trap, too, were measured in the calibrated system, as well as the gases from the other traps.

Analyses of all products were made by gas chromatography. The results obtained in these examples demonstrate the effect of subatmospheric partial pressures and the use of diluents, and are summarized in Table A. In this table, $P_{MeOH}$ designates the inlet partial pressure (absolute) in atmospheres.

TABLE A

| Example No. | 1 | 2 | 3 | 4 | 5 | 6 | 7 | 8 | 9 | 10 | 11 |
|---|---|---|---|---|---|---|---|---|---|---|---|
| Conditions | | | | | | | | | | | |
| LHSV (MeOH), hr$^{-1}$ | 0.06 | --- | --- | --- | 1 | --- | --- | --- | 12 | --- | --- |
| $P_{MeOH}$, atm | 0.04 | 1 | 0.47 | 0.25 | 0.17 | 0.07 | 0.04 | 0.50 | 0.50 | 0.25 | 0.08 |
| $P_{Total}$, atm | --- | --- | --- | --- | 1 | --- | --- | --- | 1 | --- | --- |
| Diluent | N$_2$ | none | --- | --- | N$_2$ | --- | —N$_2$ | CH$_4$ | N$_2$ | N$_2$ | --- |
| Total Product, wt% | | | | | | | | | | | |
| Hydrocarbons | 47.22 | 40.52 | 41.09 | 40.96 | 37.27 | 47.29 | 45.18 | 38.92 | (43.16)$^a$ | 44.01 | 37.13 |
| Water | 48.72 | 59.11 | 58.65 | 58.89 | 62.68 | 52.61 | 54.62 | 60.74 | 56.29 | 53.99 | 41.91 |
| H$_2$ + CO + CO$_2$ | 3.91 | 0.34 | 0.25 | 0.13 | 0.04 | 0.07 | 0.05 | 0.15 | 0.25 | 0.09 | 0.25 |
| Methanol | 0.15 | 0.03 | 0.01 | 0.02 | 0.01 | 0.03 | 0.15 | 0.19 | 0.30 | 1.72 | 10.37 |
| Dimethyl ether | — | — | — | — | — | — | — | — | — | 0.19 | 10.34 |
| Hydrocarbons, wt% | | | | | | | | | | | |
| Ethene | 21.32 | 3.16 | 4.50 | 12.41 | 17.40 | 20.98 | 13.26 | 17.46 | 11.06 | 15.86 | 12.85 |
| Propene | 20.28 | 4.78 | 8.48 | 18.16 | 26.50 | 38.71 | 47.98 | 32.90 | 34.44 | 38.20 | 42.71 |
| Butenes | 4.65 | 2.24 | 3.89 | 6.32 | 7.55 | 18.52 | 20.63 | 11.69 | 14.37 | 11.98 | 13.53 |
| Pentenes | 0.51 | 0.44 | 0.81 | 0.32 | 0.70 | 2.38 | 4.90 | 1.71 | 3.80 | 3.52 | 3.43 |
| Total C$_5$ + olefins | 46.76 | 10.62 | 17.68 | 36.89 | 52.15 | 80.59 | 86.77 | 63.76 | 63.67 | 69.56 | 72.52 |
| Methane | 1.47 | 1.46 | 1.25 | 0.84 | 0.56 | 0.51 | 0.17 | 2.31 | (3.35)$^a$ | 1.05 | 0.55 |
| Ethane | 1.22 | 2.13 | 1.33 | 1.15 | 0.67 | 0.26 | 0.11 | 0.70 | 2.60 | 0.29 | 0.16 |
| Propane | 16.90 | 17.55 | 19.19 | 18.41 | 11.04 | 4.52 | 2.40 | 9.16 | 3.86 | 4.82 | 3.90 |
| Isobutane | 18.30 | 13.51 | 10.17 | 13.97 | 8.94 | 6.98 | 5.18 | 7.99 | 4.81 | 5.82 | 6.77 |
| n-Butane | 3.20 | 4.24 | 2.44 | 3.09 | 1.61 | 1.22 | 0.66 | 1.69 | 0.69 | 0.98 | 0.85 |
| Pentanes | 4.12 | 5.64 | 2.86 | 3.05 | 2.05 | 2.62 | 2.57 | 2.68 | 2.24 | 3.19 | 3.53 |
| Total C$_5$ − paraffins | 45.21 | 44.53 | 37.24 | 40.51 | 24.87 | 16.11 | 11.09 | 24.53 | 17.55 | 16.15 | 15.76 |
| C$_6$ + PON | 1.30 | 3.89 | 2.48 | 2.26 | 2.72 | 1.31 | 1.85 | 3.72 | 8.90 | 6.59 | 7.26 |
| Aromatics | 6.73 | 40.96 | 42.60 | 20.34 | 20.26 | 1.99 | 0.29 | 7.99 | 9.88 | 7.70 | 4.46 |
| Durene in hydrocarbons | 0.04 | 0.53 | 0.30 | 0.06 | 0.12 | 0.02 | — | 0.13 | 0.30 | 0.13 | 0.22 |

$^a$ Net hydrocarbons, estimated assuming no loss.

EXAMPLE 12-14

In these examples, an HZSM-5 catalyst similar to those used in Examples 1-11 was used, under the same or similar conversion conditions except that the conversion temperature was maintained at about 700° F instead of about 800° F. The results are summarized in Table B.

TABLE B

| Example No. | 12 | 13 | 14 |
|---|---|---|---|
| Conditions | | | |
| LHSV (MeOH), hr$^{-1}$ | 1 | 1 | 1 |
| $P_{MeOH}$, atm | 0.5 | 12.9 | 0.04 |
| $P_{Total}$, atm | 12.9 | 12.9 | 1 |
| Diluent | N$_2$ | none | N$_2$ |
| Total Product, wt% | | | |
| Hydrocarbons | 44.42 | 42.04 | 46.42 |
| Water | 55.42 | 56.93 | 52.56 |
| H$_2$ + CO + CO$_2$ | 0.15 | 0.32 | 0.21 |
| Methanol | 0.01 | 0.55 | 0.81 |
| Dimethyl ether | — | 0.16 | — |
| Hydrocarbons, wt% | | | |
| Ethene | 3.46 | 0.61 | 10.22 |
| Propene | 6.93 | 1.50 | 42.44 |
| Butenes | 4.28 | 1.46 | 20.45 |
| Pentenes | 0.15 | 0.69 | 4.86 |
| Total C$_5$ − olefins | 14.82 | 4.26 | 77.97 |
| Methane | 0.14 | 1.05 | 0.07 |
| Ethane | 0.74 | 1.11 | 0.08 |
| Propane | 19.10 | 12.75 | 2.64 |
| Isobutane | 26.10 | 13.45 | 8.55 |
| n-Butane | 5.71 | 5.27 | 0.63 |
| Pentanes | 11.81 | 9.43 | 3.77 |
| Total C$_5$ − paraffins | 63.60 | 43.06 | 15.74 |
| C$_6$ + $_{PON}$ | 4.43 | 13.38 | 3.91 |
| Benzene | 0.21 | 0.81 | |
| Toluene | 1.80 | 4.28 | |
| Ethylbenzene | 0.24 | 0.90 | |
| Xylenes | 6.09 | 12.94 | |
| A$_9$ | 6.69 | 13.80 | |
| Durene | 0.66 | 2.99 | |
| Other A$_{10}$ | 1.43 | 3.39 | |
| A$_{11}$ + | 0.05 | 0.19 | |
| Total aromatics | 17.15 | 39.30 | 2.38 |

EXAMPLES 15-19

These examples were obtained with HZSM-5 catalysts with silica to alumina ratios of 40 and 140, respectively. Conversion temperatures were all about 800° F, and the other procedures and conditions were the same or similar to those used for Examples 1-11. The results are summarized in Table C.

TABLE C

| Example No. | 15 | 16 | 17 | 18 | 19 |
|---|---|---|---|---|---|
| SiO$_2$/Al$_2$O$_3$ Ratio | 40 | 40 | 140 | 140 | 140 |
| Conditions | | | | | |
| LHSV (MeOH), hr$^{-1}$ | 1 | 12 | 1 | 12 | 12 |
| $P_{MeOH}$, atm | 0.50 | 0.50 | 0.47 | 0.49 | 0.50 |

TABLE C-continued

| Example No. | 15 | 16 | 17 | 18 | 19 |
|---|---|---|---|---|---|
| $SiO_2/Al_2O_3$ Ratio | 40 | 40 | 140 | 140 | 140 |
| $P_{Total}$, atm | 1 | 1 | 1 | 1 | 1 |
| Diluent | $N_2$ | $N_2$ | $N_2$ | $N_2$ | $H_2O$ |
| Total Product, wt% | | | | | |
| Hydrocarbons | 38.76 | 44.64 | 42.46 | 40.67 | 45.99 |
| Water | 60.74 | 54.71 | 57.44 | 59.22 | (52.09)[a] |
| $H_2 + CO + CO_2$ | 0.49 | 0.63 | 0.10 | 0.10 | 0.15 |
| Methanol | 0.01 | 0.02 | TR | 0.01 | 1.75 |
| Dimethyl ether | — | — | — | — | 0.02 |
| Hydrocarbons, wt% | | | | | |
| Ethene | 1.72 | 10.79 | 7.68 | 12.13 | 12.78 |
| Propene | 3.52 | 17.74 | 15.40 | 35.46 | 33.75 |
| Butenes | 1.79 | 7.22 | 9.85 | 18.18 | 13.80 |
| Pentenes | 0.10 | 0.87 | 1.66 | 3.87 | 3.77 |
| Total $C_5^-$ olefins | 7.13 | 36.62 | 34.59 | 69.64 | 64.10 |
| Methane | 1.86 | 4.47 | 0.65 | 1.90 | 1.56 |
| Ethane | 0.98 | 0.64 | 0.48 | 0.31 | 0.24 |
| Propane | 20.78 | 11.84 | 10.23 | 3.39 | 3.80 |
| Isobutane | 16.30 | 13.08 | 13.30 | 3.71 | 5.40 |
| n-Butane | 3.70 | 5.02 | 3.27 | 0.74 | 0.69 |
| Pentenes | 4.12 | 3.95 | 4.51 | 2.23 | 2.74 |
| Total $C_5^-$ paraffins | 47.74 | 39.00 | 32.44 | 12.28 | 14.43 |
| $C_6^+$ PON | 1.90 | 2.81 | 10.33 | 9.41 | 12.40 |
| Aromatics | 43.23 | 21.57 | 22.64 | 8.67 | 9.07 |
| Durene in hydrocarbons | 0.54 | 0.32 | 0.13 | 0.13 | 0.44 |

[a]Net water, estimated assuming no Loss.

EXAMPLE 20

Ethanol was contacted with an HZSM-5 catalyst at about 800° F, at an inlet partial pressure of 0.5 atmospheres absolute, and at a feed rate of 12 LHSV. Nitrogen diluent was used to give a total pressure of about 1 atmosphere absolute. The ethanol was substantially completely converted to a hydrocarbon mixture with the following composition:

| | Wt.% | Wt.% |
|---|---|---|
| Ethylene | 34.0 | — |
| Propylene | 23.1 | — |
| Butenes | 11.2 | — |
| Pentenes | 2.3 | — |
| TOTAL $C_2$–$C_5$ OLEFINS | | 70.6 |
| TOTAL $C_1$–$C_5$ PARAFFINS | | 15.5 |
| TOTAL OTHER HYDROCARBONS | | 13.9 |
| | | 100.0 |

EXAMPLE 21

HZSM-11 was used as catalyst. Methanol was fed at an inlet partial pressure of 0.5 atmospheres absolute along with 0.5 atmospheres of nitrogen diluent. At a reaction temperature of 800° F and a LHSV of 12, substantially all (99%) of the methanol was converted to hydrocarbons. Analyses of the total effluent made by the procedures of Examples 1–11 gave the following composition:

| | Wt.% | Wt.% |
|---|---|---|
| Ethylene | 12.6 | — |
| Propylene | 32.4 | — |
| Butenes | 11.4 | — |
| Pentenes | 3.9 | — |
| TOTAL $C_2$–$C_5$ OLEFINS | | 60.3 |
| TOTAL $C_1$–$C_5$ PARAFFINS | | 16.4 |
| AROMATICS AND OTHER HCs. | | 23.3 |
| | | 100.0 |

EXAMPLE 22

A synthetic mordenite, having a silica to alumina ratio of about 93, was substituted for the HZSM-11 catalyst of Example 21. Otherwise, the experiment and reaction conditions were comparable. It was found that 76.7 wt.% of the methanol feed was converted to hydrocarbons, the composition of which was:

| | Wt.% | Wt.% |
|---|---|---|
| Ethylene | 9.7 | — |
| Propylene | 29.5 | — |
| Butenes | 14.9 | — |
| Pentenes | 2.5 | — |
| TOTAL $C_2$–$C_5$ OLEFINS | | 56.6 |
| TOTAL $C_1$–$C_5$ PARAFFINS | | 22.5 |
| AROMATICS AND OTHER HCs. | | 20.9 |
| | | 100.0 |

What is claimed is:

1. In a method for converting a feed to light olefins, said feed comprising one or more compounds selected from the group consisting of the lower monohydric alcohols with up to four carbon atoms and their simple and mixed ether derivatives, said method comprising: passing said feed at a space velocity of about 1.0 to about 50 L.H.S.V. over a catalyst contained in a reaction zone, said catalyst comprising a crystalline aluminosilicate zeolite having a constraint index of 1.0 to 12.0, a silica to alumina ratio of at least about 12 and a dried crystal density in the hydrogen form of not substantially less than about 1.6 grams per cubic centimeter, with the temperature in said reaction zone at about 500° F to about 1000° F; withdrawing from said reaction zone an effluent comprising a conjunct mixture of light olefins, paraffin hydrocarbons and aromatic hydrocarbons; and segregating said light olefins from said effluent; the improvement, whereby increasing the selectivity for said light olefins, which comprises:
   passing said feed over said catalyst at subatmospheric inlet partial pressure of said feed, referred to alcohols, of about 0.1 p.s.i.a. to about 12 p.s.i.a.

2. The improved method described in claim 1, including adding to said feed a substantially inert diluent selected from the group consisting of water, steam, nitrogen, hydrogen, carbon dioxide, and a paraffin hydrocarbon having from 1 to 5 carbon atoms, and maintaining the total pressure in said reaction zone at 15 p.s.i.a. to 500 p.s.i.a.

3. The improved method described in claim 2 wherein said feed comprises methanol of dimethyl ether.

4. The improved method described in claim 2 wherein said feed comprises ethanol.

5. The improved method described in claim 2 wherein said catalyst comprises a crystalline aluminosilicate zeolite selected from the group consisting of HZSM-5, HZSM-11, HZSM-12, HZSM-21, HZSM-35 and HZSM-38; and wherein said subatmospheric inlet partial pressure of said feed, referred to alcohols, is about 0.8 p.s.i.a. to about 7.5 p.s.i.a.

6. The improved method described in claim 5 wherein said feed comprises methanol or dimethyl ether.

7. The improved method described in claim 6 wherein said catalyst comprises HZSM-5.

8. The improved method described in claim 6 wherein said catalyst comprises HZSM-11.

9. The improved method described in claim 2 wherein said passing of said feed over said catalyst is done at a space velocity and a temperature effective to convert at least 85 weight percent of said feed to said conjunct mixture of light olefins, paraffin hydrocarbons and aromatic hydrocarbons prior to said segregation of said light olefins.

10. In a method for converting methanol to light olefins comprising ethylene, propylene and butenes, said method comprising: passing said methanol at a space velocity of about 1.0 to about 50 L.H.S.V. over a catalyst contained in a reaction zone, said catalyst comprising a crystalline aluminosilicate zeolite having a constraint index of 1.0 to 12.0, a silica to alumina ratio of at least about 12 and a dried crystal density in the hydrogen form of not substantially less than about 1.6 grams per cubic centimeter, with the temperature in said reaction zone at about 500° F to about 1000° F; withdrawing from said reaction zone an effluent comprising said light olefins mixed with paraffin hydrocarbons and aromatic hydrocarbons; and segregating said light olefins from said effluent; the improvement, whereby increasing the selectivity for said olefins, which comprises:

passing said methanol over said catalyst at subatmospheric inlet partial pressure of methanol of about 0.1 p.s.i.a. to about 12 p.s.i.a.

11. The improved method described in claim 10 wherein said inlet partial pressure of methanol is about 0.8 p.s.i.a. to about 7.5 p.s.i.a.

12. The improved method described in claim 10 wherein said crystalline aluminosilicate zeolite is HZSM-5.

13. The improved method described in claim 12, including passing over said catalyst and with said methanol, as diluent, water, steam, nitrogen, carbon dioxide or a paraffin hydrocarbon having from 1 to 5 carbon atoms, and maintaining the total pressure in said reaction zone at 15 p.s.i.a. to 500 p.s.i.a.

14. The improved method described in claim 13 wherein said diluent is water.

15. The improved method described in claim 13 wherein said diluent is steam.

16. The improved method described in claim 13 wherein said diluent is nitrogen.

17. The improved method described in claim 13 wherein said diluent is methane.

18. The improved method described in claim 13 wherein said methanol is passed over said catalyst at a space velocity and temperature effective to convert at least 85% of said methanol to said light olefins, paraffin hydrocarbons and aromatic hydrocarbons prior to said segregation step.

19. The improved method described in claim 13 wherein said methanol is passed over said catalyst at a combination of inlet partial pressure of methanol, temperature and space velocity effective to form a major fraction of light olefins in said effluent mixture.

* * * * *

UNITED STATES PATENT AND TRADEMARK OFFICE
CERTIFICATE OF CORRECTION

PATENT NO. : 4,025,575
DATED : May 24, 1977
INVENTOR(S) : Clarence D. Chang and William H. Lang It is certified that error appears in the above-identified patent and that said Letters Patent are hereby corrected as shown below:

| | |
|---|---|
| Column 1, line 57 | after word mixed "either" should be -- ether -- |
| Column 4, line 44 | after word "transformations" and before word "aliphatic" -- of -- is omitted |
| Column 4, lines 51 & 52 | Entire sentence "This activity even with silica to alumina ratios exeeding 30." in error - does not belong in patent. |
| Column 5, line 9 | "art" should be -- at -- |
| Column 7, line 16 | after word "possibly" -- because -- is omitted |
| Column 7, line 19 | "100°F" should be -- 1000°F -- |
| Column 7, line 21 | "100°F" should be -- 1000°F -- |
| Column 7, line 28 | "100°F" should be -- 1000°F -- |
| Column 7, line 59 | after word "criteria" -- are -- is omitted |
| Column 8, lines 15 & 16 | "with a relatively" appears twice. Should appear only once. |
| Column 9, Table A | Under Conditions - "Diluent" in Examples 7, 8, 9, 10 and 11 are incorrect. They should be -- |

| Example No. | | | | |
|---|---|---|---|---|
| 7 | 8 | 9 | 10 | 11 |
| -- | $N_2$ | $CH_4$ | $N_2$ | $N_2$ |

UNITED STATES PATENT AND TRADEMARK OFFICE
CERTIFICATE OF CORRECTION

PATENT NO. : 4,025,575

DATED : May 24, 1977

INVENTOR(S) : Clarence D. Chang and William H. Lang

It is certified that error appears in the above-identified patent and that said Letters Patent are hereby corrected as shown below:

Column 13, Claim 3      after word methanol "of" should be -- or --

Signed and Sealed this

Thirtieth Day of May 1978

[SEAL]

Attest:

RUTH C. MASON
Attesting Officer

LUTRELLE F. PARKER
Acting Commissioner of Patents and Trademarks